US006447816B1

(12) United States Patent
Vail, III et al.

(10) Patent No.: US 6,447,816 B1
(45) Date of Patent: Sep. 10, 2002

(54) METHODS AND APPARATUS TO PREVENT COLDS, FLUS, AND INFECTIONS OF THE HUMAN RESPIRATORY SYSTEM

(75) Inventors: William Banning Vail, III; Marilyn L. Vail, both of Bothell, WA (US)

(73) Assignee: Inhalation, Inc., Woodinville, WA (US)

( * ) Notice: Subject to any disclaimer, the term of this patent is extended or adjusted under 35 U.S.C. 154(b) by 0 days.

(21) Appl. No.: 09/542,703

(22) Filed: Apr. 3, 2000

(51) Int. Cl.$^7$ ................................................ A61K 35/78
(52) U.S. Cl. ...................... 424/742; 424/404; 424/725; 424/769; 514/957
(58) Field of Search ........................... 424/195.1, 404, 424/725, 742, 769; 426/597; 514/888, 957

(56) References Cited

U.S. PATENT DOCUMENTS 4,955,945 A * 9/1990 Weick
5,578,338 A * 11/1996 Shimabukuro

FOREIGN PATENT DOCUMENTS

JP 11209265 * 8/1999

OTHER PUBLICATIONS

Blumental et al., The Complete German Commission E Monographs: Therapeutic Guide to Herbal Medicines, p267, "Fixed combinations of eucalyptus oil and pine needle oil, published Jul. 14, 1993", American Botanical Council, USA, 1998.*
Balch et al., Prescription for Nutritional Healing, 2nd ed., pp144 and 167–8, Avery Publishing Group, Garden City Park, NY, 1997.*
Hoffman, D., The Complete Illustrated Herbal, Barnes & Noble Inc., USA. 1996, p. 185.*
Carson et al., J Applied Bacteriology (1995), 78:264–269. Antimicrobial activity of the major components of the essential oil of *Melaleuca alternifolia*.*
Cookson et al., J Antimicrobial Chemotherapy (1995), 35:421–424. Susceptibility of methicillin–resistant *Staphylococcus aureus* to the essential of *Melaleuca alternifolia*.*
Sherry, et al., "Alternative for MRSA and Tuberculosis (TB): Eucalyptus and Tea–Tree Oils as New Topical Antibacterials", 2002 Annual Meeting of the American Academy of Orthopaedic Surgeons, Feb. 13–17, 2002, Dallas, TX, Poster Board No. P376.
Anderson, "Mosby's Medical Dictionary", Fourth Edition, pp. 1476–1477, Mosby–Year Book, Inc., St. Louis, MO, 1994.
McGuffin, et. al., "American Herbal Products Association's Botanical Safety Handbook", pp. 155–157, CRC Press, New York, NY, 1997.
Patterson, et. al., "Reduced susceptibility of *Staphylococcus aureus* to vancomycin—a review of current knowledge" pp. 1–6, Communicable Disease Intelligence, vol. 23 No. 3, Apr. 20, 1999.

Anderson, "Mosby's Medical Dictionary", Fourth Edition, pp. 99–100, 102, 107, and 1173, Mosby–Year Book, Inc., St. Louis, MO, 1994.
Audesirk et al., "Biology, Life on Earth", Fourth Edition, pp. 427–429, and 522–523, Prentice Hall, Upper Saddle River, NJ, 1996.
Balch et al., "Prescription for Nutritional Healing", Second Edition, pp. 69, 77, 167–169, 209–211, 277, 346–348, and 428–430, Avery Publishing Group, Garden City Park, NY, 1997.
Fugh–Berman, "Alternative Medicine, What Works", pp. 3–16, and 192–194, Williams & Wilkins, Baltimore, MD, 1997.
Hans Dieter Knoch, "Tea Tree Export—Typical Analysis", pp. 1–3, ttexport@nrg.com.au, Mar. 9, 2000.
Hawken, "Natural Cold and Flu Defense", pp. 5–30, Woodland Publishing, Pleasant Grove, UT, 1997.
Hodges et al., "Component Analysis of Eucalyptus Oil by Gas Chromatography–Fourier Transform–Infrared Spectrometry–Mass Spectrometry", Journal of Chromatographic Science, pp. 345–350, vol. 29(8), Aug. 1991.
Hoffmann, "The Herbal Handbook", p. 95, Healing Arts Press, Rochester, VT, 1998.
Hoffmann, "The Complete Illustrated Holistic Herbal", pp. 184–187, Element Books, Inc., 1996.
Igram, "Killed on Contact, The Tea Tree Oil Story: Nature's Finest Antiseptic", pp. 1–18, and 51–61, Literary Visions Publishing, Inc., Cedar Rapids, IA, 1992.
Kohn et al., "To Err Is Human, Building a Safer Health System, Advance Copy", pp. 1–14, Institute for Medicine, National Academy Press, Washington D.C., 1999.
Lawless, "Tea Tree Oil", pp. 3–29 and 111–114, Harper Collins Publishers, Hammersmith, London, U.K., 1994.
Lawless, "The Illustrated Encyclopedia of Essential Oils", pp. 139–141, Barnes & Noble Books, New York, NY, 1999.
Luckmann, "Saunders, Manual of Nursing Care", pp. 921–929, W.B. Saunders Company, Philadelphia, PA, 1997.
Martin et al., "A Dictionary of Biology", Third Edition, p. 31, Oxford University Press, New York, NY, 1996.
Miller et al., "Ayurveda & Aromatherapy, The Earth Essential Guide to Ancient Wisdom and Modern Healing", pp. 251–252, Lotus Press, Twin Lakes, WI, 1995.

(List continued on next page.)

*Primary Examiner*—Christopher R. Tate
*Assistant Examiner*—Michele C. Flood

(57) ABSTRACT

Strong vapors from eucalyptus oil and tea tree oil are inhaled periodically to prevent the infection of the human respiratory system by pathogens that cause colds, influenza, pneumonia, and tuberculosis. Apparatus suitable for the periodic inhalation of strong vapors from eucalyptus oil and tea tree oil are provided.

5 Claims, 1 Drawing Sheet

OTHER PUBLICATIONS

Murray et al., "An Encyclopedia of Natural Medicine", pp. 227–231, Prima Publishing, Rocklin, CA, 1991.

Olsen, "Australian Tea Tree Oil Guide", pp. 14–16, Kali Press, Pagosa Springs, CO, 1991.

Olsen, "Australian Tea Tree Oil Guide", Third Edition, pp. 10–13, and 82–84, Kali Press, Pagosa Springs, CO, 1997.

Roberts et al., "Asthma: An Alternative Approach", pp. 133–137, Keats Publishing, Inc., New Canaan, CT, 1997.

Rose, "375 Essential Oils and Hydrosols", pp. 77–78, Frog Limited, Berkeley, CA, 1999.

Schnaubelt, "Advanced Aromatherapy, The Science of Essential Oil Therapy", pp. 31–41, and 96–124, Healing Arts Press, Rochester VT, 1998.

Swords et al., "Composition of Australian Tea Tree Oil (*Melaleuca Alternifolia*)", pp. 734–737, Journal of Agricultural Food Chemistry, vol. 26, No. 3, 1978.

Tenney, "Aromatherapy, Essential Oils for Essential Health", pp. 5–26, Woodland Publishing, Pleasant Grove, UT, 1997.

The Seattle Times, "Medical Digest—Protein could beat cholesterol as indicator of heart risk", Friday, Mar. 24, 2000.

Weinstein, "Asthma, The Complete Guide to Self–Management of Asthma and Allergies for Patients and Their Families", pp. 1–357, A Fawcett Crest Book, The Ballantine Publishing Group, New York, NY, 1988.

Williams, "New Uses for An Age–Old Therapy", pp. 25–27, Alternatives For the Health Conscious Individual, vol. 8, No. 4, Oct. 1999.

* cited by examiner

METHODS AND APPARATUS TO PREVENT COLDS, FLUS, AND INFECTIONS OF THE HUMAN RESPIRATORY SYSTEM

BACKGROUND OF THE INVENTION

One of the inventors has poor respiratory health, has had repeated bouts with pneumonia, colds, flu, asthma, and has been recently diagnosed with the initial stages of emphysema—despite all that modern medicine has had to offer. This first inventor also comes from a family known for a long history of respiratory problems. Therefore, the inventors decided to look beyond conventional "modern medicine" to help the first inventor, and as a result, have conceived methods to substantially prevent colds, flus, and infections of the human respiratory system. These methods include the inhalation of the vapors from eucalyptus oil and/or tea tree oil that are theorized to form a protective, and infection-preventing, thin layer within the entire respiratory system, including the lungs, bronchial tubes, and the nasal cavities. This thin layer maintains its anti-pathogenic properties for a period of time following the inhalation of the vapors for at least one-half hour, and perhaps longer. This thin anti-pathogenic layer substantially prevents the initial infection of colds, flus, and other pathogens for a period of time following inhalation. The inventors also propose the prophylactic use of inhaled eucalyptus oil and/or tea tree to prevent additional pathogenic infections such as tuberculosis, which is becoming a major health problem in the United States.

1. Field of the Invention

The field of invention relates to the prevention of colds, flus, and other pathogens within the respiratory system of human beings by the inhalation of vapors from highly volatile essential oils such as eucalyptus oil and/or tea tree oil. Following the inhalation of the vapors, a thin anti-pathogenic layer is formed in the respiratory system that protects against infection for a certain duration of time following inhalation.

2. Description of the Prior Art

While certain medical uses for eucalyptus oil and tea tree oil have been previously disclosed, to the inventor's best knowledge, none of those previously disclosed methods have suggested, or proposed, that the periodic inhalation of eucalyptus oil and/or tea tree oil may be used as prophylactic agents to substantially prevent infection of colds, flus, and other pathogens within the respiratory system of human beings for a duration of time following that inhalation. AFTER the infection of human beings with certain pathogens, previous inhalation therapies have suggested using eucalyptus oil and or tea tree oil to aid in the recovery from certain respiratory diseases. However, none of these previous methods have suggested using eucalyptus oil and/or tea tree oil as prophylactic agents to routinely and substantially PREVENT the initial infection of pathogens for a duration of time following their inhalation as a primary method of preventing disease.

SUMMARY OF THE INVENTION

An object of the invention is to provide methods to prevent the initial infection of pathogens within the human respiratory system by the inhalation of vapors from eucalyptus oil or from any of its constituents.

Another object of the invention is to provide methods to prevent the initial infection of pathogens within the human respiratory system by the inhalation of vapors from tea tree oil or from any of its constituents.

Yet another object of the invention is to prevent respiratory infections from pathogens including bacteria, viruses, and fungi.

And yet another object of the invention is provide methods to substantially prevent diseases such as colds and flus.

Yet another object of the invention is to provide methods to substantially prevent all varieties of pneumonia.

Yet further, another object of the invention is to provide methods to substantially prevent the spread of tuberculosis.

And finally, another object of the invention is to provide an inhaler apparatus conveniently made to provide vapors from essential oils such as eucalyptus oil and/or tea tree oil for inhalation into the human respiratory system.

DESCRIPTION OF THE PREFERRED EMBODIMENTS

Figure 1:
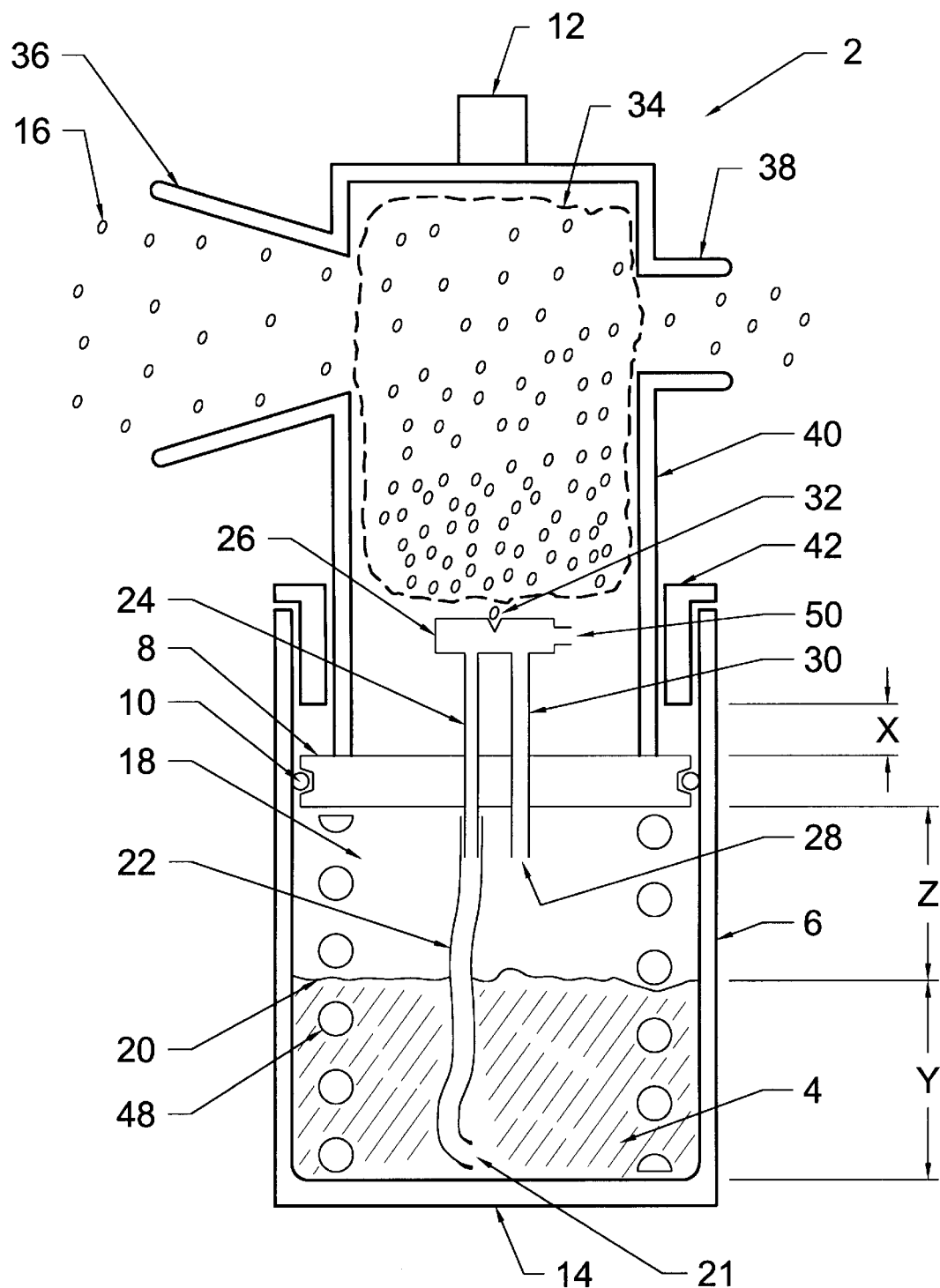
FIG. 1 shows a section view of a hand-held atomizer apparatus to produce vapors from eucalyptus oil and/or tea tree oil for inhalation to prevent pathogens from infecting the human respiratory system.

Following a business trip to Houston several years ago, the first inventor, W. Banning Vail, Ph.D., returned to Seattle and caught a dreadful form of flu. During this severe illness, the first inventor spent several weeks gasping for breath and nearly died. After several trips to a pulmonary specialist, it was found that about ⅓ of the first inventor's lung capacity had been "eaten up" by some sort of infectious agent. Therefore, the first inventor was diagnosed with a form of emphysema.

The physician further informed the first inventor that if one more such infectious episode should occur, and should that episode result in another ⅙ or more of the first inventor's lung capacity being "eaten up" by an infectious agent, then the first inventor would thereafter become a good candidate for use of oxygen tanks. Further, the first inventor was also diagnosed with asthma. The physician provided additional warnings of potential disaster in light of the first inventor's many childhood bouts with pneumonia that left scars on the lungs. Such warnings were also compounded by the first inventor's stupid habit of smoking, which he quite some 20 years ago.

The first inventor's father, William Banning Vail, Jr., had emphysema, and had used oxygen tanks for perhaps five years. Accordingly, the first inventor feared emphysema and the use of oxygen tanks. The terms such as "emphysema", "asthma", and related diseases are defined and described in Weinstein, 1988, an entire copy of which is incorporated herein by reference. The clinical manifestations of emphysema, asthma, and other respiratory infections are defined and described in Luckmann, 1997, an entire copy of which is incorporated herein by reference.

For many years, it seems almost every time that the first inventor had taken an airplane flight, or had otherwise gone into a public place with a large number of people, he had often caught a cold, a flu, or some other "bug". The terms such as "cold", "flu", "infectious disease", "pathogen" "pathogens", "pathogenesis", "pathologic microorganisms", etc., are defined in Anderson, et. al., 1994, an entire copy of which is incorporated herein by reference. Here, colds include diseases caused by any strain of a rhinovirus. Here, flus include diseases caused by any type of influenza, including those of the respiratory system. Therefore, the first inventor came to fear airplane flights, being in places with many people, etc. because of fear of being infected again with pathogens that could possible result in death by terminal emphysema.

In Anderson, et. al, 1994, on page 808, the term "risk for infection" is defined as "a state in which an individual is at increased risk for being invaded by pathogenic organisms". Anderson, et. al, 1994, page 808, further states: "Risk factors include inadequate primary defenses, such as broken skin, traumatized tissue, decrease in ciliary action, . . . , tissue destruction, . . . ".

Luckmann, 1997, page 868, also states under the topic of "Nonspecific Body Defenses Against Infection", and under "1. Physical barriers" the following:

"a. Physical, or anatomic, barriers are the 1st line of defense against infection." and "b. Physical barriers include intact skin and mucous membranes lining the respiratory, gastrointestinal and genitourinary tracts."

Therefore, Luckmann, 1997 specifically refers to the mucous membranes lining the respiratory system as being important to prevent infection, and any less than optimum condition of these membranes would provide another "risk factor" favoring infection by some pathogen.

The first inventor has set forth an hypothesis that his respiratory system and lungs are subject to such "risk factors", and that the first inventor had to invent a new method to prevent invasion by such pathogenic organisms. Consequently, the first inventor has concluded that to minimize the possibility of ending up on oxygen tanks, that it is necessary to prevent the infection of his respiratory system by common pathogens such as pathologic bacteria, viruses, and fungi. It is clear that any one of these pathogens may cause disease. However, the first inventor has the additional hypothesis, that in analogy with many biological systems, it is likely that human diseases can also be caused by a combination of such pathogens that form symbiotic relationships, similar to well-documented mycorrhizal relationships or the like, which may also change in time. For a description of such mechanisms in biology, for example see Audesirk and Audesirk, 1996 on these and related subjects. Therefore, from the first inventor's point of view, it is possible that any one disease may involve bacteria, viruses, and fungi all at one time, and the mix of these may change vs. time as the disease progresses through various stages.

From the first inventor's point of view, many of his illnesses had begun with either cold-like symptoms or flu-like symptoms. If he got very sick, this often progressed into symptoms mimicking those of pneumonia. So, an initial predominant viral-like infection may evolve into a predominantly bacterial-like infection as time progresses. So, the first inventor views the development of some diseases as progression of various stages, where any one stage may have a peculiar mix of pathogens. The progression of colonies of pathogens vs. time may in fact involve viral, bacterial, and fungal elements called for the purposes herein "symbiotic pathogens" that may make "symbiotic pathogenic colonies". Typically, the composition of those "symbiotic pathogentic colonies" vary with time. As has often been the case in the past, when the first inventor had problems with his respiratory system, standard antibiotics rarely helped. In the first inventor's view, this is because the antibiotics only addressed part of the problem in a typically complex case when "symbiotic pathogens" are causing disease that has at least two components among the three that are viral, bacterial, and fungal components. The view that a given disease is often caused by a time varying mix of bacterial, viral, and fungal pathogens provides the precise reason why the first inventor rarely found commercial antibiotics to be of effective help in overcoming his various lung diseases. Accordingly, the first inventor has theorized that to be able to routinely prevent colds, flus, etc., it is necessary to locate substances that have antiviral and antibacterial and antifungal elements that may be applied to the respiratory system simultaneously.

The first inventor further hypothesized that microscopic portions of his respiratory system at any one time are subject to increased risk of invasion by such pathogens. Any such increased risk site for the purposes herein is defined as a "likely pathogenic invasion site". Once a pathogen "invades" such a "likely pathogenic invasion site", for example within tissue within the lungs, then the pathogens may multiply, causing an infection that may "eat away" the lungs of the first inventor. The first inventor has concluded that he needs new methods and apparatus to prevent or block the invasion of pathogens into a likely pathogenic invasion site within his respiratory system. Put another way, the first inventor sought to find a practical method to reduce the risk of infection of the respiratory system by infectious agents.

This is a tall order. The first inventor had theorized about using certain face masks, filtering the air inhaled by the lungs, and passing inhaled air through U.V. light (with the energy of the U.V. below the threshold to produce ozone). Then, the first inventor decided to investigate inhaled chemicals to prevent the invasion by pathogens of a likely pathogenic invasion site. Such chemicals need to be highly volatile, non-toxic, and capable of killing bacteria, viruses, and fungi. The second inventor, Marilyn L. Vail, suggested using eucalyptus oil and/or tea tree oil as potential candidates because of her prior research on these substances in her attempts to control *Candida albicans*.

The inventors identified a class of chemical compounds that may be used to prevent the invasion of pathogens into the respiratory system. They include eucalyptus oil and tea tree oil. The first inventor has found that routinely inhaling these substances has prevented him from getting any colds, flus, or pneumonia during the last 6 months of his personal experiments. This is truly remarkable, because the first inventor has often been sick every several months or so during the last several years.

The first inventor performed experiments on himself with very crude apparatus. A small bottle of "eucalyptus rectified essential oil" made by "aroma-vera" was purchased. It had a blockage near the top of the bottle. Typically, the first inventor shook the bottle with the blockage "down" which caused eucalyptus oil to catch in the blockage near the top of the bottle. Then, with the bottle held with the blockage "up", and while holding one nostril closed, the first inventor would inhale very deeply through the other nostril thereby inhaling concentrated vapors of eucalyptus oil. Then the process was repeated with the other nostril. The first inventor estimates that the amount inhaled ranged between 0.001 milligrams to 100 milligrams, depending upon the circumstances, and the number of repetitions. The first inventor performed this inhalation immediately before he went "into public", such as into an enclosed public area having one or more human beings within that enclosed area. If there were sick people present that were coughing, or otherwise admitted that they had a cold, the flu, or pneumonia, the first inventor would thereafter similarly inhale concentrated vapors of eucalyptus oil every 30 minutes or so. By following this process, the first inventor has not had a cold, the flu, or pneumonia during the entire winter season spanning late 1999 and early 2000.

The first inventor alternatively used tea tree oil in the above experiments and had similar results. The tea tree oil was in a small bottle marked with the legend "100% PURE AUSTRALIAN TEA TREE OIL" made by Desert Essence.

It is important to note that very strong vapors of either eucalyptus oil or tea tree oil were inhaled each time. This happened because of the close proximity of the nose to a pool of highly volatile fluids. However, there were several drawbacks to this method. As a first drawback, on occasion the fluids themselves got sucked up into the nose causing a very unpleasant situation. As a second drawback, if the fluids got on the hands, and then into the eyes, this was also an extraordinarily unpleasant, and perhaps, a dangerous situation. As a third drawback, inhalation through the mouth seemed relatively ineffective from vapors emanating from a simple bottle. Accordingly, the inventors have designed an apparatus that provides very strong vapors that may be inhaled, but which also overcomes the above first, second and third drawbacks.

FIG. 1 shows a section view of an apparatus to conveniently generate vapors from eucalyptus oil that may be inhaled without suffering the above three drawbacks. Eucalyptus oil is chosen for this preferred embodiment, but the use of other suitable essential oils, such as tea tree oil, are discussed below. The apparatus in FIG. 1 is described as a hand-held "atomizer" that is generally designated with element 2. Eucalyptus oil 4 is shown in container 6. A piston 8 having O-ring 10 seals against the interior of the container wall. The atomizer has top element 12 that acts as a "button" (hereinafter "top button 12"), and the container has bottom 14. With one hand, placing the middle finger on the button 12 and the thumb on the bottom 14, and squeezing, produces the vaporized droplets of eucalyptus oil. One such droplet of eucalyptus oil is designated by numeral 16 that is shown in the location to be inhaled by the user.

The vapors of eucalyptus oil may be inhaled through the mouth, or through the nose, or through both. Holding one nostril closed at a time allows selective inhalation through one nostril, and then the other, so that the entire respiratory system may be entirely coated with the thin anti-pathogenic film of eucalyptus oil.

In FIG. 1, the atomizer is to be operated "substantially vertically" a term that will be defined below. Pressing down on button 12 increases the air pressure in air pocket 18 above the surface of the eucalyptus oil 20. This increasing pressure causes eucalyptus oil to flow through first entrance 21 of flexible tube 22 and then to first tube 24 that is in turn connected to the atomizer assembly 26. The first entrance 21 of the flexible tube is reinforced and constructed so that it does not collapse under use, and does not make a positive seal against the interior of the container walls that would interfere with functionality. Pressurized air flows thorough second entrance 28 of the second tube 30 that is in turn also connected to the atomizer assembly 26. Using typical designs for atomizers, and the like, the flow of eucalyptus oil and pressurized air into the atomizer assembly 26 generates particles of eucalyptus oil in the form of a vapor that pass through the exit passage 32 of the atomizer assembly. The atomizer assembly 26 may have any number of suitable valves, one-way valves, spring actuated valves, spring return valves, ball valves, spring loaded ball valves, breather orifices, etc., which are used in the art to make atomizers, and the like, for the purposes herein, however, those elements are not shown in FIG. 1 solely for the purposes of brevity. Any suitable "atomizer means" may be used for atomizer assembly 26.

In FIG. 1, the vaporized eucalyptus oil is injected from the exit passage 32 of the atomizer assembly into a cotton ball 34 whose edges are delineated with dashed lines in FIG. 1. Therefore, pushing down on button 12 causes vapors of eucalyptus oil to be injected into the cotton ball. Then, the vapors diffuse through the cotton ball for subsequent inhalation.

The tapered mouth orifice 36 is used to inhale vaporized eucalyptus oil by mouth. As vaporized eucalyptus oil and air is inhaled, any additional air required is provided through nostril orifice 38.

Alternatively, nostril orifice 38 is used to inhale vaporized eucalyptus oil by one nostril at a time. One nostril is held shut, and the other one is placed against nostril orifice 38 to inhale through a chosen nostril. One after another, both nostrils may be used to suitably inhale vapors of eucalyptus oil.

Other details are shown in FIG. 1. The upper body of the hand-held atomizer 40 is a one-piece unit having tapered mouth orifice 36 and nostril orifice 38. The upper body is attached to the piston 8 using typical fabrication techniques. The spacer 42 is designed to guide the main body 40 during its motion, and it serves as a retainer to prevent the piston 8 from inadvertently coming out of the container 6. The spacer 42 may also have one or more check-valves to function as "breathers" when the unit is initially filled with eucalyptus oil, respectively enumerated as 44 and 46, however these elements are not shown in FIG. 1 solely for the purpose of brevity. Spacer 42 has suitably close tolerances, or threads as necessary, to positively engage it to container 6.

FIG. 1 shows the position of piston 8 wherein the top portion of that piston is a distance designated by the legend "X" below the lower portion of the spacer 42. As the top button 12 is pushed downward, the piston 8 is also pushed downward thereby compressing spring 48, and the vaporized droplets of eucalyptus oil are formed. The "down stroke" causes the top of the piston to move through a maximum, and extreme value, of X. After completing the "down stroke", and upon removing finger pressure from the button, then compression spring 48 returns the top portion of the piston so as to make contact with the lower portion of the spacer 42, which is the "resting position" of the piston. Typical breather holes, one-way valves, such as ball valves, etc., are used to allow air to flow back into air pocket 18, thus preparing for the next "down stroke". Such a breather hole for the purposes herein is shown as element 50 that is located within a portion of atomizer assembly 26. In the "up stroke", and in this embodiment, air can flow into breather hole 50, and thereafter flow through second tube 30 to air pocket 18 thereby allowing the piston to return to its "resting position". Without such a breather hole, or the like, the piston might permanently stay in the "down stroke" position, or might stay in that position until other air leakages allowed the top of the piston to again contact the bottom portion of spacer 42. To achieve this functionality, various different preferred embodiments contemplate using any number of suitable valves, one-way valves, spring actuated valves, spring return valves, ball valves, spring loaded ball valves, breather orifices, etc., which are used in the art to make atomizers, and the like.

In FIG. 1, refilling the atomizer involves removing the spacer 42, removing the piston 8 from the container 6, and refilling the container. The piston 8 is then inserted into the container 6, and the spacer is reinstalled. Yet one or more ball valves in the piston (not shown) may be used to bleed off extra pressure in the event that is necessary during installation of the piston. Any such pressure relief valves shall have the numerals 52 and 54 respectively, but they are not shown in FIG. 1 solely for the purposes of brevity.

The hand-held atomizer overcomes several of the problems cited earlier. In relation to the above defined "first drawback", by using the cotton ball and the apparatus described, no fluids can get sucked up into a nostril. In relation to the above defined "second drawback", no liquids are generated exterior to the hand-held atomizer, so there is minimal chance of getting eucalyptus oil into the eyes. Further, the cotton ball also prevents liquids from being squirted directly into the eyes. In relation to the third drawback, the hand-held atomizer provides proper vaporized eucalyptus oil for inhalation by mouth. Therefore, the inventors have designed an apparatus and provided methods of operation that provide very strong vapors that may be inhaled, but which also overcome the previously defined first, second and third drawbacks.

There are many variations on the above preferred embodiment. The container 6 may be fabricated from any suitable material, including any type of plastic, or any type of transparent or translucent plastic of any coloration. Transparent or translucent plastics are convenient so that the presence or absence of the eucalyptus oil, and the surface of the eucalyptus oil 20, may be easily determined by visual inspection. The upper body of the hand-held atomizer 40 having tapered mouth orifice 36 and nostril orifice 38 may be made of any suitable material, including any type of plastic, or any type of transparent or translucent plastic of any coloration. Transparent or translucent plastics are convenient to determine the condition and extent of the cotton ball 34.

For proper operation, the cotton ball 34 should substantially fill and make contact with the interior walls of the upper body of the hand-held atomizer 40. The cotton ball 34 is convenient, but any material may be used as a substitute that has "cotton-ball like qualities" for the purposes of the invention herein that otherwise also avoids the above defined first, second, and third drawbacks. No toxic materials may be used to replace the cotton-ball. Spacer 42 may be fabricated from any material and may be disposed in its location in FIG. 1 using any suitable attachment methods including friction fitting, matching threads, retainer notches, and the like. Any suitable "retainer means" may replace spacer 42.

The dimensions of the nostril orifice 38 are chosen so that it conveniently extends beyond the radial extent of the container 6 and into the nostril for use when held in place by the fingers. The exterior of the container 6 has a first radius R1 (not shown in FIG. 1) that is typically ½ inches, and a first vertical length, or extent, L1 (not shown in FIG. 1) that is typically 1¾ inches tall. Here, the radius is defined as the radial distance away from the vertical axis of the container 6. For the record, FIG. 1 is not to scale. The nostril orifice 38 has a second radial extent R2 (not shown in FIG. 1) that is typically 1¼ inches and a nostril orifice diameter NOD (not shown in FIG. 1) that typically ranges between 3/16 inches O.D. to ¼ inches O.D. for convenient insertion into the nose, but many other dimensions are possible. The diameter NOD is chosen so that the nostril orifice can go into the interior of a typical nostril.

The tapered mouth orifice 36 has a third radial extent R3 (not shown in FIG. 1) that is typically 1½ inches, and an mouth inhalation diameter MID (not shown in FIG. 1) that is typically 1½ inches OD. The tapered mouth orifice may not be circular, and may be any suitably chosen shape to conveniently fit into the mouth. The overall maximum vertical dimension of the hand-held "atomizer", which is the distance between the button 12 and the bottom 14, is typically 3 inches.

In the above, it was stated that the atomizer is to be operated "substantially vertically". The atomizer is to be held in a "substantially vertical orientation" for proper operation. The definition of these terms are as follows. For proper operation, the first entrance 21 of the flexible tube must be immersed in the fluid 4, and must be located below the fluid level 20 so that fluid may be properly atomized ("first condition"). In the above embodiment, the second entrance 28 of the second tube is used to provide air under pressure to the atomizer assembly 26, so that the second entrance 28 must also be located above the fluid level 20 so for proper atomization of the fluid ("second condition"). Lastly, various means, including breather holes and suitable valves, have been described which allow the piston to return from the "down stroke" to its "resting position", and consequently, the orientation of the atomizer in FIG. 1 should be sufficiently vertical so as not to interfere with such means ("third condition"). Any hand-held "atomizer" that is generally designated with element 2 in FIG. 1 that is an orientation such that the first, second, and third conditions are satisfied in this paragraph is in a position that is "substantially vertical". Accordingly, the atomizer is operated "substantially vertically" which is in a "substantially vertical orientation". In general, when the atomizer is held in the hand, its longitudinal axis along its length is at an angle θ with respect to true vertical (which angle is not shown in FIG. 1 for brevity). This longitudinal axis is parallel to the vertical sides of the container 6. The maximum "tilt angle" at which the atomizer fails to meet the first, second, and third conditions depends upon the particular distance from the interior of the bottom of the container to the top of the fluid level 20, when the atomizer is held in the true vertical position, and that particular distance is identified by the legend Y in FIG. 1. Accordingly, there is reason to maintain a reasonable distance between the top of the fluid and the bottom of the piston, and that reasonable distanced is defined by the legend Z in FIG. 1. When X achieves its maximum value in the "down stroke" (XMAX) then Z maintains its minimum value at that position (ZMIN) for any given level of fluid in the container Y for θ=0 degrees. The variables XMAX, ZMIN and θ are not shown in FIG. 1 for the purposes of simplicity. The above comments may be suitably reformulated in terms of the volume of the fluid 4 inside the container 6. For future reference, the inside diameter of the container 6 is the parameter IDC, that is not shown in FIG. 1 for the purposes of brevity.

In earlier disclosure, element 16 was identified as a droplet of eucalyptus oil. There are two additional comments here. First, as is typical with most atomizer devices, there is a statistical distribution of droplet sizes and volumes produced depending upon a number of factors including the fluid, its viscosity, the design of the atomizer system, and the force applied to the button 12. The inventors include herein by reference all art in the field related to the production and measurements of such statistical distributions of droplet sizes. Second, any droplet 16 in FIG. 1 may also stand for any other droplet of any other fluid described to this point or hereafter in this application.

There are other variations of the apparatus. The functional elements in FIG. 1 may be reconfigured to fit onto a screw-on cap that in turn screws onto a bottle having eucalyptus oil. The bottle may in fact be the original bottle of eucalyptus oil that arrived from a manufacturer, so that the refilling process becomes easier. However, this is a minor variation of the invention, and in the interests of brevity, shall not be described in detail.

Tea tree oil may be substituted in the above for eucalyptus oil. Put another way, element 4 in FIG. 1 may be chosen to be tea tree oil instead. The use of tea tree oil in the apparatus is similar, except that it is possible that the atomizer assembly 26 may be changed because of the different properties that tea tree oil may have, including different viscosity, density, vapor pressure, etc. Each atomizer assembly may be specifically designed for the oil to be atomized. Each atomizer, or "atomizer means", may in fact be specific to different suppliers of tea tree oil or eucalyptus oil in that different suppliers may produce oils having different characteristics as they affect vaporization by the atomizer.

Yet further, element 4 may be chosen to be pure eucalyptus oil; pure tea tree oil; any mixture of eucalyptus oil and tea tree oil; any mixture of one or more components from eucalyptus oil and one or more components from tea tree oil (which components are defined below); any mixture of eucalyptus oil and distilled water; any mixture of tea tree oil and distilled water; and any mixture of eucalyptus oil, tea tree oil, and distilled water; and any mixture of the following—(a) one or more components from eucalyptus oil and (b) one or more components from tea tree oil and (c) any percentage of distilled water. Therefore, element 4 may be chosen to be any of the above defined fluids in FIG. 1.

Now, several additional topics are discussed below as they relate to the invention respectively entitled "Baseline Activities"; "Composition of Eucalyptus Oil"; "Comments About Eucalyptus Oil"; "Composition of Tea Tree Oil"; "Comments About Tea Tree Oil"; "Essential Oils"; "Eucalyptus Oil, Tea Tree Oil, and Prevention of Infections of Circulatory System and Prevention of Heart Attacks"; "Methods to Reduce Infections Following Operations"; 'The Phrase "To Prevent"'; and "References".

Baseline Activities

During the experiments lasting some six months described earlier, the first inventor also did some other "baseline activities" that were important to maintain good lung health. To control his asthma, he inhaled twice a day Alupent® and Flovent® for the typical medical reasons. Further, the first inventor raised the head of his bed by about 4 inches to prevent gastric juices and related gasses from entering the respiratory system while sleeping. It may turn out that these "baseline activities" are important to the methods set forth in preferred embodiments of this invention. Usual experimental techniques will be used to determine their importance if necessary. As another statement of fact, the first inventor most often inhaled eucalyptus oil, but also often inhaled tea tree oil during this trial period. Another aspect of the invention includes the method of using eucalyptus oil and/or tea tree oil in combination with the use of Alupent® and Flovent® to prevent colds, flus, and pneumonia in individuals having asthma.

Composition of Eucalyptus Oil

The chemical composition of eucalyptus oil is complicated and is known. There are various varieties, including oil from Eucalyptus australiana. See Hedges and Wilkens, 1991, an entire copy of which is incorporated herein by reference describes oil from that species. Page 345 of this reference states in part:

"Analysis of Eucalyptus oil, like that of any complex mixture, presents difficult problems not only in the separation but also in identification of components. Terpenes and terpene derivatives constitute the bulk of the oil (1,2) and, due to the inherent flexibility of the isoprene units which comprise the compounds, the oil contains many closely related isomers and homologs. Further characterization reveals that 40–80% of the oil is composed of one compound, 1,8-cineole, thus presenting the choromatographer with a large sample dynamic range problem."

Hedges and Wilkens, 1991, on page 345, further state:

"A Eucalyptus australiana oil sample was obtained . . . ".

Hedges and Wilkens, 1991, on page 346, further state:

"Fifty-eight peaks were counted in the chromatogram of E. Australiana."

Hedges and Wilkens, 1991, on page 347, in "Table 1. Component identification by CG-IR-MS*" list the following compounds as being present, or likely present, in Eucalyptus oil: α-pinene; 1,8-cineole; limonene; α-terpinene; 2,3-dimethylcyclohexanol; cis-linalool oxide; terpinolene; ρ-cymenene; α-pinene oxide; linalool; isopentyl isovalerate; fenchyl alcohol; α-campholenal; 3,3,6,6-tetramethyltricyclo [3.1.0.02.4]hexane; trans-verbenol; 2,5-dimethyl benzaldehyde; borneol; 4-terpineol; 1-methyl phenyl ethanone; α-terpineol; α-hexyl cinnamaldehyde; 4-isopropenyl-1-methy cyclohexenel; para-mentha-1(7),8,10-dien-9-ol; ρ-carvone; 1-methylethyl-2-methylene cyclohexanone; geraniol; isoborneol acetate; α-terpinenyl acetate; β-patchoulene; geranyl η-propionate; β-gurjunene; aromadendrene; and allo-aromadendrene. Different preferred embodiments of this invention contemplate using one or more of the above components in any proportion to achieve the desired results. Further, all routine techniques used in the medical and biological sciences are incorporated herein by reference, and these standard techniques may be used to identify one or more of the above compounds as being the active ingredients to obtain the desired results. Once so identified, the individual compound or mixture of compounds are merely different preferred embodiments of the invention disclosed herein.

Further information concerning the detailed chemical analysis of eucalyptus oil are provided in references 1–25 on page 350, of Hedges and Wilkens, 1991, and entire copies of all such 25 references are incorporated herein by reference.

An earlier reference, Gunther, 1948, provided an older list of ingredients of eucalyptus oil. An entire copy of Gunther, 1948, is incorporated herein by reference. In particular, see pages 437–525, of Volume IV of this reference. For different varieties of eucalyptus oils, and sources for those oils, please also see Schnaubelt, 1998; Lawless, 1999; and Rose, 1999; entire copies of which are incorporated herein by reference.

Comments about Eucalyptus Oil

Balch and Balch, 1997, page 69, state under "Action and Uses" for eucalyptus oil the following: "Clears congestion, has a mild antiseptic action, and reduces swelling by helping to increase blood flow. Relaxes tired and sore muscles. Good for colds, coughs, and other respiratory disorders." This reference on page 69, also states under "Comments" concerning eucalyptus oil: "Recommended for external use only. It should not be used on broken skin or open cuts or wounds."

Miller and Miller, 1995, state on page 251, the following: "Eucalyptus is one of the most commonly used essential oils. You could write a book on all its uses. There are over 700 varieties of eucalyptus, some growing to 500 feet, and they all possess similar properties. It is currently used in many allopathic medical preparations. It is one of the three best oils for use with any respiratory tract problems because the component eucalyptol is mucolytic (it relaxes the flow of mucous) and it excretes the eucalyptol out though the lung surface. Even if you take it internally in tea form, eucalyptus will very quickly pass out of the body through the lungs, having its relaxing effect to the mucous membranes. As it is inhaled it gives an immediate effect; then again as it circulates out of the body." This reference further recites certain additional formulas "including rosemary and camphor". This reference further states with regards to "Actions": "diaphoretic, decongestant, stimulant, antiseptic, antispasmodic, alternative, diuretic, expectorant, antipyretic, regenerative, lowers blood sugar, disinfects the air, increases concentration, deodorant, germicidal".

Fugh-Berman, 1997, on page 194, states the following warnings about potential toxicity: "Essential oils should only be taken orally under the supervision of a practitioner experienced in their use. Tea Tree oil and eucalyptus oil have been associated with childhood poisonings, [Jacobs, Webb] and ingestion of pennyroyal oil has killed at least two adults. [Sullivan, Vallance] Essential oils are safe to use topically if diluted (and a few are safe full-strength)." These references are listed below under "References" so that the interested reader can further investigate the toxicity of eucalyptus oil and other essential oils.

Only AFTER the inventors had conceived the inventions herein, and only AFTER the personal trials conducted by the first inventor had been completed, the inventors found a hard-to-locate newsletter entitled "Alternatives For the Health Conscious Individual", written by Dr. David G. Williams. In particular in the October, 1999 issue of Williams, 1999, on page 25, Dr. Williams states in part: "The essential oil extracted from the leaves has long been used in cough drops and cold medications, mouthwashes, toothpaste, detergents, and liniments for arthritis pain." This reference further states on page 25: "In fact, millions of people take advantage of eucalyptus'antimicrobial properties each day by swishing with that old medicine chest staple, Listerine." That reference on page 25, also states: "Thanks in large part to the eucalyptus, Listerine is a very potent germ-killer . . . " This article further states that Listerine® "can kill 60 percent of the HIV virus it touches within 30 seconds. In this same time period, Listerine® killed 100 percent of the bacteria *Staphylococcus aureus* present."

Williams, 1999, page 26, then recounts several anecdotal stories. In one, and during a trip to Australia when "the winter flu season was in full swing", he noticed that almost everyone he "encountered had succumbed to this flu with the notable exception of two cleaning ladies" each of which "carried a small rag that had been doused with the oil of eucalyptus". In their presence, the "fumes were very strong . . . ".

Williams, 1999, page 26, then recounts a discussion with the above cleaning ladies: "When I questioned the ladies, they told me that one of their grandfathers had used eucalyptus oil to ward of flu since World War I. At that time, a military base had apparently experienced a flu epidemic so sever the soldiers were dying from it. To stop the problem, authorities sealed off one of the barracks and sprayed down the interior with eucalyptus oil. Then they placed all the solders in that building for a day. That action reportedly stopped the epidemic in 24 hours."

Williams, 1999, page 26,further states: "Eucalyptus oil can be toxic if taken internally, but breathing the oil's fumes will likely allow its bactericidal components to knock out infections in the nasal passages, sinuses, bronchial tubes, and lungs." Williams, 1999, page 26, then suggests by analogy to carrying around rags soaked with eucalyptus oil that it "can actually prevent the flu", but he gives no mechanism for doing so, and provides no methods of doing so —except carrying around rags soaked with eucalyptus oil or soaking a room like the barracks with the oil. Williams, 1999, page 26, further states: "I'am currently investigating a very unusual eucalyptus variety that is non-toxic when taken orally. If it checks out, this development will open up all kinds of fantastic medicinal possibilities." Apparently, Dr. Williams is primarily concerned with orally taken medication.

Therefore, Williams, 1999, states or implies that eucalyptus oil may be effective against certain viruses and against certain bacteria. However, the methods set forth in Williams, 1999, of providing such vapors to human beings are not practical in their normal lives. Normal human beings cannot carry around rags soaked with eucalyptus oil that would produce odors offensive to others. Nor is it practical to lock people up in a barracks or other rooms washed down with eucalyptus oil. Several preferred embodiments of this invention are provided to overcome these problems.

Williams, 1999, does NOT describe the methods or apparatus disclosed in the preferred embodiments herein. Williams, 1999, does not describe directly inhaling the fumes periodically from an inhalant device as a method to prevent infection. Williams, 1999, does not describe any type of thin anti-pathogenic layer or barrier that substantially prevents the initial infection of colds flus, and other pathogens for a period of time following the inhalation of eucalyptus oil. Williams, 1999, does not describe the proposed use of eucalyptus oil as a prophylactic agent to prevent the initial infection of tuberculosis. Williams, 1999, does not describe methods of infection proposed by the inventor involving a "likely pathogenic invasion site", and the use of inhaled vapors of eucalyptus oil to decrease the risk of invasions or infections of such sites by pathogens. Nor does Williams, 1999, describe the possibility that infectious diseases may involve the progression of colonies of pathogens vs. time that may involve viral, bacterial, and fungal elements defined earlier as "symbiotic pathogens", and that the initial infection of these pathogens may be prevented by the periodic inhalation of strong vapors from eucalyptus oil.

Further, Williams, 1999, does not describe any method to reduce the risks of infection of the human respiratory system by pathogens that includes at least the step of the inhalation of concentrated vapors from eucalyptus oil immediately before entering an enclosed public area having one or more human beings within said enclosed area.

Still further, Williams, 1999, does not describe the method to prevent the initial infection of the human respiratory system by pathogens causing diseases such as colds, flus and pneumonia, that includes at least the step of inhaling concentrated vapors of eucalyptus oil to form an anti-pathogenic barrier inside the human respiratory system that is effective for a period of time of at least 30 minutes following said inhalation. Nor does Williams, 1999, describe periodic inhalations of vapors from eucalyptus oil to maintain the anti-pathogenic barrier inside the human respiratory system.

Another reference, Igram, 1992, page 18, states the following:

"Eucalyptus oil is used for the purpose of healing the respiratory passages, and the amount that actually entered the tissues is minimal."

Schnaubelt, 1998, describes in on pages 31–40, and elsewhere, the antibacterial, antiviral, and antifungal effects of certain essential oils. For example, Schnaubelt, 1998, page 33, refers to another study which showed that various essential oils had varying effectiveness against different pathogens including "Pneumococcus spec., *Klebsiella* pneumoniae, Staphylococcus aureus haemolyticus, Neisseria catarrahalis, Streptococcus haemolyticus, Proteus vulgaris, Haemophilus influenzae, Haemophilus pertusis" and "Candida albicans, and Escherichia coli-Aerobacter group, various Cornybacteria, Listeria".

Composition of Tea Tree Oil

The chemical composition of tee tree oil is complicated and is known. See Swords and Hunter, 1978, an entire copy of which is incorporated herein by reference. Page 734 of this reference states in part:

"Australian tea tree oil (*Melaleuca alternifolia*) was fractionated by column chromatography and analyzed by combined gas chromatograhy-mass spectrometry. Preparative GLC of selected fractions yielded pure compounds for analysis by infrared and nuclear magnetic resonance spectroscopy. Forty compounds were identified, including viridiflorene which has not previously reported as occurring in nature." Swords and Hunter, 1978, on page 734–735, further state:

"The chemical composition of tea tree oil has been previously investigated by the Instrumental Laboratories of Fritzsche Brothers, Inc.; New York, and the following components were reported (Gunther, 1968): α-pinene, 2.2%; α-terpinene, 7.5%; limonene, 1.0%; 1,8-cineole, 5.6%; γ-terpinene, 17.5%; ρ-cymene, 3.0%; terpinolene, 3.1%; 1-terpinen-4-ol, 44.9%, α-terpineol, 5.2%; aromadendrene, 21.7%; two unknown sesquiterpenes, 1.6% each."

Swords and Hunter, 1978, on page 737, show "Table I" which presents the list of compounds present, or suspected to be present, in tea tree oil as follows: 1. α-Pinene; 2. Camphene; 3. β-Pinene; 4. Sabinene; 5. Myrcene; 6. α-Phellandrene; 7. 1,4-Cineole; 8. α-Terpinene; 9. Limonene; 10. 1,8-Cineole; 11. γ-Terpinene; 12. p-Cymene; 13. Terpinolene; 14. Hexanol; 15. Allyl hexanoate; 16. ρ,α-Dimethylstyrene; 17. a Sesquiterpene; 18. α-Cubebene; 19. a Sesquiterpene; 20. α-Copaene; 21. Camphor; 22. α-Gurjunene; 23. Linalool; 24. a Sesquiterpene; 25. Unidentified; 26. 1-Terpineol; 27. 1-Terpinen-4-ol; 28. β-Elemene; 29. Caryophyllene; 30. a Sesquiterpene; 31. Aromadendrene; 32. β-Terpineol; 33. Alloaromadendrene; 34. Unidentified; 35. Humulene; 36. Unidentified; 37. γ-Muurolene; 38. α-Terpineol; 39. Viridiflorene; 40. Piperitone; 41. α-Muurolene; 42. Piperitol; 43. Unidentified; 44. σ-Cadinene; 45. 4,10-Dimethyl-7-isopropyl bicyclo [4.4.0]-1,4-decadiene; 46. Nerol; 47. 8-ρ-Cymenol; and 48. Calamenene. Capital letters were used here for various compounds because they were so listed in Table 1 in Swords and Hunter, 1978. Lawless, 1994, pages 22–23, states the following:

"The Australian standard for *Melaleuca alternifolia* oil now requires that the terpinen-4-ol content of the oil should be greater than 30 per cent, and the cineole content less than 15 per cent. A top quality tea tree oil should, however, have a maximum cineole content of 5 per cent and a minimum terpinen-4-ol content of 35–40 per cent. As the demand for tea tree has increased, the essential oil has also been increasingly subjected to adulteration, usually with cineole—the main constitu ent of eucalyptus oil which gives eucalyptus oil its characteristic camphor-like scent." This reference further goes on to state: "The balance of the main constituents in a fresh, high quality tea tree oil should be approximately as follows: Alpha-pinene 2.5 per cent ; Alpha-terpinene 9.1 per cent; Para-cymene 3.9 per cent; 1,8-cineole 4.3 per cent; Gamma-terpinene 24.6 per cent; Alpha-terpineol 2.3 per cent; Terpinen-4-ol 42.1 per cent; (and) Terpinolene 4.1 per cent."

In the above quotation from Lawless, 1994, pages 22–23, the ';' and the word 'and' were added to the previous quote to make it readable solely for the purposes of brevity in accordance with rules of the USPTO for specification.

A more recent reference was obtained from the internet concerning the constituents of tea tree oil. This was obtained from the company called "Hans-Dieter Knoch Tea Tree Export" on Mar. 9, 2000 at the world-wide web address of "www.midcoast.com" that lists the following ingredients as a "Typical Analysis" from Batch No. HK008: alpha-pinene 1.3%; sabinene 1.3%; alpha-terpinene 9.4%; Limonene 1.1%; p-cymene 2.5%; 1,8 cineole 2.9%; gamma-terpinene 20.2%; terpineolene 3.4%; Terpinen-4-ol 38.2%; alpha-terpineol; 2.4%; Aromadendrene 2.4%; Ledene 1.4%; delta-cadinene 1.6%; Glubolul 0.5%; and Viridiflorol 0.4%.

Comments about Tea Tree Oil

It is of interest to note that item 21 in Table I of Swords and Hunter, 1978, (discussed above) is "Camphor", that is specified as one ingredient in Mentholatum® Ointment. However, the statement on a container of this ointment in the possession of the inventors reads as follows: "Gentle aromatics help relieve stuffy noses, chest congestion, sinus congestion, head colds, chest colds, and muscular aches due to coughs and colds." The label on the container does NOT make any statement about prevention of colds or flus by using the product.

Fugh-Berman, 1997, page 193, states the following:

"Tea tree oil is widely used as an antibacterial and antifungal topical medication, and several studies indicate its effectiveness. One compared pure tea tree oil and the antifungal drug clotrimazole for treatment of fungal infection of the toenails. After six months, the two treatments were found to be equally effective. [Buck]"

Lawless, 1994, on pages 25–26, states the following:

"Due to its unique composition, tea tree oil displays a number of remarkable properties making it very effective for a wide range of complaints..; Foremost among these properties, and what makes tea tree oil outstanding in comparison to other remedies, is that it is active against all varieties of infections organisms: bacteria, fungi and viruses. Independent microbiological testing has confirmed the effectiveness of tea tree oil against a wide range of micro-organisms, notably:

Gram Positive bacteria: *Staphyloccus aureus, Staphyloccus epidermidis, Staphyloccus pneumoniae, Staphyloccus faecalis; Staphyloccus pyrogenes, Staphyloccus agalactiae, Propionibacterium acnes, Beta haemolytic streptococcus*

Gram Negative bacteria: *Escherichia coli, Klebsiella pneumoniac*, Citrobacter spp., *Shigella sonnei, Proteus mirabilis*, Legionella spp., *Pseudomonas aeruginosa*

Fungi: *Trichophyton mentagrophytes, Trichophyton rubrum, Aspergillus niger, Aspergillus flavus, Candida albicans, Microspourm canis, Microsporum gypseum, Thermoactinomycetes vulgarism."

Lawless, 1994, page 26, further states:

"Tea tree's effectiveness in fighting infection is further backed up by its ability to stimulate the immune system—this means that if the body is threatened by any of these organisms, tea tree increases the body's own ability to protect itself and to respond appropriately. Tea tree oil's main areas of activity therefore be summarized as: antiseptic/bactericidal, anti-fungal, anti-viral, and immuno-stimulant."

Regarding the antiviral properties of tea tree oil, Lawless, 1994, page 27, states:

"Viruses are the invading organisms responsible for most epidemic illnesses. As a powerful anti-viral agent, tea tree is effective in fighting many common infectious diseases such as measles, chickenpox, flu, colds and shingles as well as other viral complaints such as cold sores, veruccae and warts."

Regarding the immuno-stimulant properties of tea tree oil, Lawless, 1994, pages 27–28, further states:

"In this context, tea tree is principally of great value as a preventative remedy—to help the body fight off all kinds of infection. This is especially important if the body is already in a weakened condition brought on by either stress, illness or the use of anti-biotics or other drugs which have lowered the body's natural resistance levels. Tea tree has been found to be especially helpful for those who need to have their strength built up, such as before a surgical operation or for those suffering from chronic or long-standing debilitating illnesses such as glandular fever or hepatitis. Its possible application to AIDS is also currently being researched."

Lawless, 1994, on pages 18–24, describes the chemical make-up of tea tree oil. On page 20, it states in part: "In its natural state, tea tree oil is an extremely complex chemical substance containing at least 48 organic compounds. The main constituents are terpenes, pinenes, cymones, terpineols, cineole, sesquiterpines and sesquiterpinene alcohols—however, it also contains four constitutions that are rarely found elsewhere in nature: viridiflorene (approximately 1 per cent), B terpineol (0.24 per cent), L-terpineol (trace) and allyhexanoate (trace). [1]" The reference cited at the end of this quote is Swords and Hunter, 1978, although the recitation is misspelled in Lawless, 1994 on page 112.

Following a percentage break-down of substances within tea tree oil, Lawless, 1994, on page 23, further states:

"It is interesting to note that none of the these substances is especially effective alone. It is only in combination that these substances demonstrate their maximum healing power—which is known as a 'synergy'. This is a quality common to many essential oils, where the unique balance of constituents, including the trace elements, contributes to the overall effectiveness of the remedy. This factor also helps to account for why synthetically produced products, or 'nature-identical' oils, cannot match properties exhibited by the naturally derived original, since it is very difficult to mimic the complex and diverse blend of components found in nature."

Igram, 1992, on page 17, states in part: "It should be emphasized that tea tree oil is an antiseptic." Igram, 1992, further states: "This is not to suggest that tea tree oil is exceptionally toxic when taken internally. There are no deaths on record from internal use or accidental overdose."

Igram, 1992, further states on page 17:

"Tea tree oil finds its greatest usage as a remedial agent for diseases affecting the exposed surfaces and mucous membranes. It can be safely used in small doses on all mucous membranes, including the gums, oral mucosa, vagina, urethra, colon and rectum. Although internal ingestion has been attempted without noticeable toxic effects, this is not enough evidence to warrant its widespread use internally."

With regards to the respiratory system, Igram, 1992, page 18, states with regard to tea tree oil: "It can be inhaled to help relive bronchial congestion and to aid in opening clogged sinus passages."

Further, tea tree oil penetrates tissues deeply. Regarding this subject, Igram, 1992, page 54, states the following:

"One of the major obstacles in eradicating Candida infections, as well as other fungal infections, is getting the medicine to penetrate deep enough into the site of the invention. If a person weeds a garden by mowing the weeds only, they will grow right back. The cure is achieved by digging the weeds out by the roots, or in today's age, destroying the roots with chemicals. In a similar manner it is crucial to utilize medicines which penetrate as deeply as possible into the skin and mucous membranes. This is precisely the advantage of tea tree oil. It has the greatest penetrating capacity of any known antifungal agent. As it saturates the tissues, it kills fungal organisms on contact."

However, Olsen, 1991, points out that under apparently comparatively rare circumstances, that there are adverse affects related to the use of tea tree oil. For example, on page 14, of Olsen, 1991, it states the following: "Tea Tree Oil was tested recently in 1991 in a family practice office. Fifty patients with various skin problems were chosen at random." The reference continues with: "One patient dropped out of the study and a second discontinued due to a mild erythematous skin sensitivity to the 100% oil. This was the only side-effect reported." The reference further states: "The results of using the Tea Tree Oil were striking. All the patients but one were cured or showed remarkable improvement of the conditions treated."

Olsen, 1997, page 11, states the following:

"ISO Standard 4730 states that tea tree oil should be extracted from *Melaleuca alternifolia, Melaleuca linafolia*, or *Melaleuca dissitifolia* species of the Myrtaceae family. Other tea tree species, including Cajuput (*Melaleuca Cajuputi*), New Zealand Manuka (*Leptospermum scoparium*), New Zealand Ti-Tree (*Cordyline australis*), and Kanuka (*Leptospermum ericoides*) are not highly regarded, as they do not contain the same anti-microbial benefits, nor have they been in use for nearly a century as has *Melaleuca alternifolia.*"

Further, Olsen, 1997, on page 12, presents typical "Analytical Results" that presents the chemical composition and percentages present for a sample from the Australian Plantations, July 17, 1997, which is incorporated herein by reference.

Yet further, Olsen, 1997, on page 83, states the following:

"Action. Pure tea tree oil conforming to Australian standard A.S.D. 175, revised 1985 (AS 2782-1985) and 1996 (ISO 4730) is a powerful broad-range antiseptic, fungicide, and bactericide. The main component is terpinen-4-ol (T-4-ol). Optimal activity at 35–40% w/v. Its bacterial actions is increased in the presence of blood, serum, pus, and necrotic tissue. It is able to penetrate deeply into infected tissue and pus, mix with these, and cause them to slough off while leaving a healthy surface. The oil has a very low toxicity, and is virtually a non-irritant event to sensitive tissues. Because of its lower cineole level, tea tree oil is less toxic and less irritating that eucalyptus oil. Be aware that some unknown eucalyptus oils have been blended with a synthetic form of terpinen-4-ol, which alters the chemical composition."

Essential Oils

The "essential oils" are defined on page 63, of Balch and Balch, 1997, as follows:

"Essential oils are derived from herbs or other plants through steam distillation or cold pressing. They are usually mixed with a vegetable oil or water, and used either as a mouth, ear, or eye wash, or as an inhalant, douche, or tea. These oils can also be used externally in massage or on burns and abrasions. Essential oils readily combine with the natural fats present in the skin. With few exceptions, such as the use of camphor, eucalyptus, or tea tree oil for certain skin conditions, essential oils should always be diluted in either water or oil before being applied to the body, and they should not be taken internally except under the direction of a physician trained in their use."

Prime examples of essential oils are eucalyptus oil and tea tree oil. In one preferred embodiment of the invention, vapors are alternatively inhaled, first from eucalyptus oil, and then from tea tree oil, to prevent colds, flu, and the like. This is the so-called "alter method" of using essential oils. The rationale for using such an approach is to avoid a build-up of immunity developed by organisms to just one substance. Further, eucalyptus oil may preferentially affect one set of pathogens, and tea tree oil may affect another set of pathogens, in a complex disease that may have bacterial, viral, and fungal elements.

Different embodiments of the invention contemplate using any essential oil known that has at least the following properties: it is non-toxic when inhaled; and it has anti-pathogenic properties. Many such essential oils are listed in Gunther, 1948; in Schnaubelt, 1998; in Lawless, 1999; in Olsen, 1997; and in Rose, 1999.

In addition to mixtures of essential oils that may substitute for element 4 in FIG. 1 that have already been listed above, element 4 in addition may be chosen to be any one of the following: any mixture of eucalyptus oil with one or more other essential oils; any mixture of tea tree oil with one or more other essential oils; any mixture of eucalyptus oil, tea tree oil, with one or more other essential oils; any mixture of eucalyptus oil, tea tree oil, one or more essential oils, and distilled water; any mixture of (a) one or more components from eucalyptus oil, (b) one or more components from tea tree oil and (c) one or more components from any other essential oil; and any mixture of (a) one or more components from eucalyptus oil, (b) one or more components from tea tree oil, (c) one or more components from any other essential oil, and (d) any portion of distilled water. Typical procedures in the art may be used to determine the optimum percentage mixtures of any of the above components to prevent colds, flus, and infections of the human respiratory system. Therefore, element 4 in FIG. 1 may include any of the above listed fluids.

For the purposes herein, the term "essential oils" include all ingredients from the plant Lomatium dissectum. This plant was referred to in Schnaubelt, 1998, on page 39, with the following quote:

"As shown by Indians of the Pacific Northwest, placing more faith in a much broader effectiveness of essential oils against viral illnesses is more justified than the paucity of scientific studies would suggest. These Indians were able to protect themselves against the devastating consequences of the worldwide flu epidemic of 1918 with a preparation made from a native plant, Lomatium dissectum[8]." Here, the superscript refers to Alstat, 1987.

Eucalyptus Oil, Tea Tree Oil, and Prevention of Infections of Circulatory System and Prevention of Heart Attacks Several studies have been performed involving the expectorant effects of various essential oils. See Schnaubelt, 1998, pages 39–40, that describes results from several other references. A relevant point for this analysis is that a "clinical study determined the terpine levels in blood of test subjects after they inhaled essential oils." That reference further states: "Within thirty to forty minutes the concentration of essential oils absorbed through inhalation sinks to half its original value. This demonstrates that there is no danger of accumulating essential oils in the body even with repeated uses."

Further, Schnaubelt, 1998, on pages 98–99, shows that the inhalation of essential oils results in essential oils being provided to the "heart-lung-circulatory system". Recent literature points to irritations, or inflammations, of the circulatory system caused by unknown pathogens as being associated with certain forms of heart disease. For example, according to page A7, of The Seattle Times, Friday, Mar. 24, 2000, researchers identified "levels of C-reactive protein (CRP)" as an indicator for heart attacks. This article states "The protein indicates if arteries are inflamed."

To my knowledge, the quoted researchers do not know what pathogens cause the inflammation in the circulatory system. However, since eucalyptus oil and tea tree oil have antibacterial, antiviral, and antifungal properties, no matter what the type of pathogen is involved, then the periodic inhaling of concentrated vapors from eucalyptus oil and/or tea tree oil may be used as an effective preventative measure against the development of this type of heart disease and the resulting heart attacks.

Therefore, inhaled vapors from eucalyptus oil and tea tree oil enter the blood stream and are useful to reduce the inflammation caused by pathogens to reduce the probability of heart attacks.

Further, a preferred embodiment of the invention is a method to reduce inflammation of the human circulatory system caused by pathogens to prevent heart attacks that includes at least the step of inhaling concentrated vapors of eucalyptus oil so that said oil enters the circulatory system, whereby said tea tree oil possesses antibacterial, antiviral, and antifungal properties useful to reduce any the inflammation.

Another preferred embodiment is the method to reduce inflammation of the human circulatory system caused by pathogens to prevent heart attacks that includes at least the step of inhaling concentrated vapors of tea tree oil so that said oil enters the circulatory system, whereby said tea tree oil possesses antibacterial, antiviral, and antifungal properties useful to reduce any the inflammation.

Similar comments apply to other essential oils that are non-toxic when inhaled, that possess antibacterial, antiviral, and antifungal properties useful to reduce any inflammation within the circulatory system.

Methods to Reduce Infections Following Operations

A major cause of deaths in hospitals in the United States are attributed to infections following operations. For example, see the book entitled "To Err is Human, Building a Safer Health System", "Advanced Copy", published by the Institute of Medicine, National Academy of Sciences, that is listed under Kohn, et. al., 1999 in the "References" below. Perhaps a dear cousin in my family fell victim recently to such an infection. A device similar to the atomizer shown in FIG. 1 could be used to reduce the probability of infection following many operations. In this case, nostril orifice 38 could be blocked off, or it could instead attached to a sterile source of flowing gas, such as air or nitrogen.

This preferred embodiment provides the method to generate and cause a mist of droplets of tea tree oil and distilled water to flow to the open wound in the human body during major surgery. The tea tree oil and distilled water mist would form an antibacterial, antiviral, and antifungal barrier against infection from the dreadful types of infections pathogens present in typical operating rooms. Other embodiments contemplate using various different mixtures of tea tree oil, other essential oils, and distilled water.

The Phrase "To Prevent"

The above disclosure has described methods to prevent the initial infection of the human respiratory system by pathogens causing diseases such as colds, flus and pneumonia, that includes at least the step of inhaling concentrated vapors of eucalyptus oil to form an anti-pathogenic barrier inside said respiratory system that is effective for a period of time of at least 30 minutes following said inhalation.

The above disclosure has also described methods to prevent the initial infection of the human respiratory system by pathogens causing diseases such as colds, flus and pneumonia, that includes at least the step of inhaling concentrated vapors of tea tree oil to form an anti-pathogenic barrier inside said respiratory system that is effective for a period of time of at least 30 minutes following said inhalation.

The above paragraphs have used the word "prevent". In typical drug tests regulated by the FDA (the Food and Drug Administration), Phase I, Phase II, Phase III, and sometimes, Phase IV trials are carried out. See page 16, of Fugh-Berman, 1997. The word "prevent" is often used herein in a statistical manner. As pointed out on pages 11–13, of Fugh-Berman, 1997, a drug must provide benefit that is "statistically significant" over the so-called "placebo effect", where subjects report improvements in up to ⅓ of the cases. In several of the preferred embodiments, the word "prevent" means to provide "statistically significant" benefits against infection over the so-called "placebo effect".

Because of the statistical nature of the word "prevent", several of the above embodiments describe methods to reduce the risks of infection of the human respiratory system by pathogens that includes at least the step of the inhalation of concentrated vapors from eucalyptus oil immediately before entering an enclosed public area having one or more human beings within said enclosed area.

In the previous paragraph, pathogens include viruses, bacteria, fungi, tuberculosis, and infectious agents causing pneumonia.

One way to conduct trials on the above methods to prevent diseases are "randomized trials". See Fugh-Berman, 1997, page 12. For example, during the next flu season, perhaps 10 children's day care centers could be chosen. Then, on a random basis, ½ of the teachers in the children's day care centers could periodically inhale eucalyptus oil and/or tea tree oil to prevent colds and flus. Then, the results could be compared to the ½ of the teachers that did not do so. Then, the same group could be swapped. Standard statistical analysis can then be used to determine the statistical effectiveness of the preventative methods.

In several embodiments above, it is stated that eucalyptus oil and/or tea tree oil provide a barrier against infection by pathogens. These barriers include a direct barrier, but also include other "barrier-like effects". The inhaled oils soak into the cells within the respiratory system that provides additional protection against infection by pathogens. The oils reduce any pre-existing infection caused by pathogens, and therefore, in conjunction with the immune system, again provides additional protection against infection by pathogens. The oils help mucous membranes repair themselves, and so this effect also provides additional protection against infection by pathogens. The oils help repair many types of existing damage and therefore, this effect also provides additional protection against infection by pathogens.

References

The above recited references are defined as follows, entire copies of which are incorporated herein by reference:

Alstat, E., in the paper entitled "Lomatium Dissectum, An Herbal Virucide", in the journal called "Complementary Medicine", May/June 1987, pages 32–33 ("Alstat, 1987") [Ed Alstat]

Anderson, K. N., Anderson, L. E., and Glanze, W. D., Editors, the book entitled "Mosby's Medical Dictionary", Fourth Edition, Mosby-Year Book Inc., St. Louis, Mo., 1994 ("Anderson, et. al., 1994")

Audesirk, T., and Audesirk, G., the book entitled "Biology, Life on Earth", Fourth Edition, Prentice Hall, Upper Saddle River, N.J., 1996 ("Audesirk and Audesirk, 1996") [Teresa Audesirk and Gerald Audesirk]

Balch, J. F., and Balch, P. A., in the book entitled "Prescription for Nutritional Healing", Second Edition, Avery Publishing Group, Garden City Park, New York, N.Y., 1997 ("Balch and Balch, 1997") [James F. Balch, M.D. and Phyllis A. Balch, C.N.C.]

Buck, D. S., Nidorf, D. M., and Addino, J. G., in the article entitled "Comparison of two topical preparations for the treatment of onychomycosis: *Melaleuca Alternifolia* (tea tree) oil and clotrimazole", in the Journal of Family Practice, Volume 38, No. 6, pages 601–605, 1994 (Buck, et. al., 1994")

Editor, article entitled "Protein could beat cholesterol as indicator of heart risk" in the section entitled "Medical Digest", The Seattle Times, Mar. 24, 2000, page A7 ("The Seattle Times, 2000")

Fugh-Berman, A., the book entitled "Alternative Medicine, What Works", Williams & Wilkins, Baltimore, Md., 1997 ("Fugh-Berman, 1997") [Adriane Fugh-Berman, M.D.]

Gunther, E., the book entitled "The Essential Oils", Volumes I, II, III, and IV, Lancaster Press, Lancaster, Pa., 1948

Hedges, L. M. and Wilkens, C. L., in the article entitled "Component Analysis of Eucalyptus Oil by Gas Chromatography-Fourier Transform-Infrared Spectrometry-Mass Spectrometry", in the publication called the Journal of Chromatographic Science, Volume 29, August, 1991 ("Hedges and Wilkens, 1991")

Igram, C., the book entitled "Killed on Contact, The Tea Tree Oil Story: Nature's Finest Antiseptic", Literary Visions Publishing, Inc., Cedar Rapids, Iowa, 1992 ("Igram, 1992") [Cass Igram, D.O.]

Jacobs, M. R., Hornfeldt, C. S., in the article entitled "Melaleuca oil poisoning", in the journal called "Clinical Toxicology", Volume 32, No. 4, pages 461–464, 1994 ("Jacobs and Hornfeldt, 1994")

Kohn, L., Corrigan, J., and Donaldson, M., Editors, the book entitled "To Err is Human, Building a Safer Health System", "Advanced Copy", Institute of Medicine, National Academy Press, Washington, D.C., 1999 (Kohn, et. al., 1999) [Linda T. Kohn, Janet M. Corrigan, and Molla S. Donaldson]

Lawless, J., the book entitled "Tea Tree Oil", Harper Collins Publishers, Hammersmith, London, U.K., 1994 ("Lawless, 1994") [Julia Lawless]

Lawless, J., the book entitled "The Illustrated Encyclopedia of Essential Oils", Barnes & Noble Books, New York, N.Y., 1999 ("Lawless, 1999") [Julia Lawless]

Luckmann, J., Editor, the book entitled "Saunders, Manual of Nursing Care", W. B. Saunders Company, Philadelphia, Pa., 1997 ("Luckmann, 1997") [Joan Luckmann, MA, RN]

Martin, E., Ruse, M., and Holmes, E., Editors, the book entitled "A Dictionary of Biology", Third Edition, Oxford University Press, New York, N.Y., 1996 ("Martin, et. al., 1996") [Elizabeth Martin MA; Michael Ruse BSc, PhD; and Elaine Holmes BSc, PhD]

Miller, L., and Miller, B., the book entitled "Ayurveda & Aromatherapy, The Earth Essential Guide to Ancient Wisdom and Modern Healing", Lotus Press, Twin Lakes, Wis., 1995 ("Miller and Miller, 1995") [Dr. Light Miller, ND, and Dr. Bryan Miller, DC]

Olsen, C., the book entitled "Australian Tea Tree Oil Guide", Kali Press, Pagosa Springs, Colo., 1991, ("Olsen, 1991") [Cynthia B. Olsen]

Olsen, C., the book entitled "Australian Tea Tree Oil Guide", Third Edition, Kali Press, Pagosa Springs, Colo., 1997 ("Olsen, 1997") [Cynthia Olsen]

Rose, J., the book entitled "375 Essential Oils and Hydrosols", Frog, Limited, Berkeley, Calif., 1999 ("Rose, 1999") [Jeanne Rose]

Schnaubelt, K., the book entitled "Advanced Aromatherapy, The Science of Essential Oil Therapy", Healing Arts Press, a division of Inner Traditions International, Rochester, Vt., 1998 ("Schnaubelt, 1998") ["Kurt Schnaubelt, Ph.D."]

Sullivan, J. B., Rummack, B. H., and Thomas, H., in the article entitled "Pennyroyal oil poising and hepatoxicity", in the Journal of the American Medical Association, Volume 242, No. 26, pages 2873–74, 1979 ("Sullivan, et. al., 1979")

Swords, G. and Hunter, G. L. K., in the article entitled "Composition of Australian Tea Tree Oil (*Melaleuca alternifolia*)" presented in the Journal of Agricultural Food Chemistry, Volume 26, No. 3, 1978, pages 734–737 ("Swords and Hunter, 1978")

Vallence, W. B., the article entitled "Pennyroyal poisoning: a fatal case", in the journal called "Lancet", Volume 2, pages 850–851, 1955 ("Vallence, 1955")

Webb, N. J., and Pritt, W. R., in the article entitled "Eucalyptus oil poisoning in childhood: 41 cases in southeast Queensland", in the journal called "Journal of Paediatrics and Child Health", Volume 29, pages 368–371, 1993 ("Webb and Pritt, 1993")

Weinstein, A. M., the book entitled "Asmtha, The Complete Guide to Self-Management of Asthma and Allergies for Patients and Their Families", A Fawcett Crest Book, The Ballantine Publishing Group, New York, N.Y., 1988 ("Weinstein, 1988") [Allen M. Weinstein, M.D.]

Williams, D. G., in the article entitled "New Uses for An Age-Old Therapy", in the newsletter called "Alternatives For the Health Conscious Individual", Vol. 8, No. 4, October, 1999 ("Williams, 1999") [Dr. David G. Williams]

In addition, each above cited references refer to yet other papers, publications, books, etc., and entire copies of each and every such document is also incorporated herein by reference in their entirety. For example, Hedges and Wilkens, 1991, cite under its "References" and item "1." a book that is entitled "The Essential Oils", Vol. I, II, and IV, by the author of E. Gunther, Lancaster Press, Lancaster, Pa., 1948, and according the previous sentence, an entire copy of that reference is incorporated herein by this statement.

While the above description contains many specificities, these should not be construed as limitations on the scope of the invention, but rather as exemplification of preferred embodiments thereto. As have been briefly described, there are many possible variations. Accordingly, the scope of the invention should be determined not only by the embodiments illustrated, but by the appended claims and their legal equivalents.

What is claimed is:

1. A method to prevent infection of the human respiratory system by *Staphylococcus aureus* for the prevention of staphylococcal pneumonia in an enclosed public area having one or more human beings within said enclosed area comprising the following steps:

(a) within a period of time of 30 minutes before entering said public area, inhaling an effective amount of the concentrated vapors from eucalyptus oil; and (b) after entering said public area, periodically inhaling the concentrated vapors from eucalyptus oil, whereby the period of time between successive inhalations exceeds 30 minutes, and whereby the period of time between successive inhalations is less than 2 hours; and (c) inhaling an effective amount of the concentrated vapors from tea tree oil at least one time per day.

2. A method to reduce the risks of infection of the human respiratory system by *Staphylococcus aureus* in an enclosed public area having one or more human beings within said enclosed area comprising the following steps:

(a) within a period of time of 30 minutes before entering said public area, inhaling an effective amount of the concentrated vapors from eucalyptus oil; and (b) after entering said public area, periodically inhaling the concentrated vapors from eucalyptus oil, whereby the period of time between successive inhalations exceeds 30 minutes, and whereby the period of time between successive inhalations is less than 2 hours; and (c) inhaling an effective amount of the concentrated vapors from tea tree oil at least one time per day.

3. A method to reduce the risks of infection of the human respiratory system by *Staphylococcus aureus* in an enclosed public area having one or more human beings within said enclosed area comprising the following steps:

(a) within a period of time of 30 minutes before entering said public area, inhaling the concentrated vapors from a mixture comprising 50% of eucalyptus oil and 50% tea tree oil; and (b) after entering said public area, periodically inhaling the concentrated vapors from said mixture, whereby the period of time between successive inhalations exceed 30 minutes, and whereby the period of time between successive inhalations is less than 2 hours.

4. A method to reduce the risks of infection of the human respiratory system by *Staphylococcus aureus* in an enclosed public area having one or more human beings within said enclosed area comprising the following steps:
 (a) within a period of time of 30 minutes before entering said public area, inhaling from a hand-held atomizer apparatus the concentrated vapors from a mixture of 50% comprising eucalyptus oil and 50% tea tree oil; and
 (b) after entering said public area, periodically inhaling from said hand-held atomizer apparatus said concentrated vapors from said mixture, whereby the period of time between successive inhalations exceeds 30 minutes, and whereby the period of time between successive inhalations is less than 2 hours; and
 whereby said concentrated vapors are generated within said hand-held atomizer apparatus; and
 whereby said concentrated vapors are inhaled through at least one orifice attached to said hand-held atomizer apparatus.

5. A method to reduce the risks of infection of the human respiratory system by *Staphylococcus aureus* in an enclosed public area having one or more human beings within said enclosed area comprising the following steps:
 (a) within a period of time of 30 minutes before entering said public area, inhaling the concentrated vapors from a mixture comprising 50% of eucalyptus oil and 50% tea tree oil, whereby said concentrated vapors are generated within a hand-held atomizer apparatus; and whereby said concentrated vapors are inhaled through at least one orifice attached to said handheld atomizer apparatus; and
 (b) after entering said public area, periodically inhaling the concentrated vapors from said mixture in said hand-held atomizer apparatus, whereby the period of time between successive inhalations exceeds 30 minutes, and whereby the period of time between successive inhalations is less than 2 hours.

\* \* \* \* \*